US008835667B2

(12) United States Patent
Shinohara et al.

(10) Patent No.: US 8,835,667 B2
(45) Date of Patent: *Sep. 16, 2014

(54) ELECTROLYTE FORMULATIONS (75) Inventors: Hiromi Shinohara, Kanagawa Pref. (JP); Kentaro Kawata, Kanagawa Pref. (JP); Hiroki Yoshizaki, Mitaka (JP); Peer Kirsch, Seeheim-Jugenheim (DE); Nikolai (Mykola) Ignatyev, Duisburg (DE); Michael Schulte, Bischofsheim (DE); Jan Sprenger, Rommerskirchen (DE); Maik Finze, Nienburg (DE); Walter Frank, Wuppertal (DE)

(73) Assignee: Merck Patent GmbH, Darmstadt (DE)

( * ) Notice: Subject to any disclaimer, the term of this patent is extended or adjusted under 35 U.S.C. 154(b) by 231 days.

This patent is subject to a terminal disclaimer.

(21) Appl. No.: 13/522,545

(22) PCT Filed: Jan. 12, 2011

(86) PCT No.: PCT/EP2011/000089
§ 371 (c)(1),
(2), (4) Date: Jul. 17, 2012

(87) PCT Pub. No.: WO2011/085965
PCT Pub. Date: Jul. 21, 2011

(65) Prior Publication Data
US 2012/0309982 A1    Dec. 6, 2012

(30) Foreign Application Priority Data
Jan. 18, 2010   (EP) ..................... 10000405

(51) Int. Cl.
C07F 5/02       (2006.01)
H01G 9/20       (2006.01)
H01M 10/056     (2010.01)
H01L 51/00      (2006.01)

(52) U.S. Cl.
CPC ............. C07F 5/02 (2013.01); H01G 9/2031 (2013.01); H01G 9/2059 (2013.01); Y02E 10/542 (2013.01); H01M 10/056 (2013.01); H01G 9/2004 (2013.01); H01L 51/0086 (2013.01); Y02E 10/52 (2013.01)
USPC ....................................... 558/384

(58) Field of Classification Search
CPC ........................................ C07F 5/02
USPC ........................................ 558/384
See application file for complete search history.

(56) References Cited

U.S. PATENT DOCUMENTS

| | | | |
|---|---|---|---|
| 5,350,644 A | 9/1994 | Graetzel et al. | |
| 6,586,670 B2 | 7/2003 | Yoshikawa | |
| 6,861,722 B2 | 3/2005 | Graetzel et al. | |
| 7,208,626 B2 | 4/2007 | Welz-Biermann et al. | |
| 7,632,969 B2 | 12/2009 | Welz-Biermann et al. | |
| 8,114,318 B2 | 2/2012 | Kuang et al. | |
| 2002/0040728 A1 | 4/2002 | Yoshikawa | |
| 2004/0238826 A1 | 12/2004 | Sekiguchi et al. | |
| 2005/0119513 A1 | 6/2005 | Ignatyev et al. | |
| 2005/0131256 A1 | 6/2005 | Welz-Biermann et al. | |
| 2007/0191637 A1 | 8/2007 | Welz-Biermann et al. | |
| 2007/0293391 A1 | 12/2007 | Finze et al. | |
| 2010/0069655 A1 | 3/2010 | Finze et al. | |
| 2010/0229950 A1 | 9/2010 | Kuang et al. | |
| 2011/0012048 A1 | 1/2011 | Zhang et al. | |
| 2012/0309981 A1* | 12/2012 | Ignatyev et al. | 548/110 |

FOREIGN PATENT DOCUMENTS

| | | |
|---|---|---|
| EP | 0 986 079 A2 | 3/2000 |
| EP | 1 180 774 A2 | 2/2002 |
| EP | 1 507 307 A1 | 2/2005 |
| WO | WO 91/16719 A2 | 10/1991 |
| WO | WO 03/087020 A1 | 10/2003 |
| WO | WO 03/087113 A1 | 10/2003 |
| WO | WO 2006/045405 A1 | 5/2006 |
| WO | WO 2007/093961 A1 | 8/2007 |
| WO | WO 2009/083901 A1 | 7/2009 |

OTHER PUBLICATIONS

Yao et al. "Organo-Tricyanoborates as Tectons: Illustrative Coordination Polymers Based on Copper(I) Derivatives" Inorganic Chemistry, 2005, vol. 44, pp. 6256-6264.*
International Search Report of PCT/EP2011/000089 (Mar. 1, 2011).
M. Gorlov et al., "Ionic Liquid Electrolytes for Dye-Sensitized Solar Cells", Dalton Transactions, (2008) pp. 2655-2666.
C.J. Barbe et al., "Nanocrystalline Titanium Oxide Electrodes for Photovoltaic Applications", J. Am. Ceram. Soc., vol. 80, No. 12 (1997) pp. 3157-3171.
R.D. Chambers et al., "Some Salts of Trifluoromethylfluoroboric Acid", J. Am. Chem. Soc., vol. 82 (Oct. 20, 1960) pp. 5298-5301.
P. Wang et al., "Enhance the Performance of Dye-Sensitized Solar Cells by Co-Grafting Amphiphilic Sensitizer and Hexadecylmalonic Acid on TiO2 Nanocrystals", J. Phys. Chem. B, vol. 107, No. 51 (2003) pp. 14336-14341.

(Continued)

Primary Examiner — Joseph Kosack
(74) Attorney, Agent, or Firm — Millen, White, Zelano & Branigan, P.C.

(57) ABSTRACT

The present invention relates to electrolyte formulations comprising at least one compound of formula (I) $M^{a+}[B(R_f)(CN)_x(F)_y]_a^-$ (I) in which Ma+ is an inorganic or organic cation, $R_f$ denotes straight-chain or branched perfluoroalkyl groups having 1 to 4 C atoms, $C_6F_5$, $C_6H_5$, partially fluorinated phenyl or phenyl which is monosubstituted or disubstituted by perfluoroalkyl groups having 1 to 4 C atoms, a is 1 or 2, x is 1, 2 or 3, y is 0, 1 or 2 and x+y is 3 and their use in an electrochemical and/or optoelectronic device such as a photovoltaic cell, a capacitor, a light emitting device, an electrochromic or photo-electrochromic device, an electrochemical sensor and/or biosensor, preferably their use in a dye or quantum dot sensitized solar cell.

14 Claims, 3 Drawing Sheets

(56) References Cited

OTHER PUBLICATIONS

G.A. Molander et al., "Improved Synthesis of Potassium (Trifluoromethyl)trifluoroborate [K(CF3BF3)]", Organometallics, vol. 22, No. 16 (2003) pp. 3313-3315.

H.J. Frohn et al., "A Preparative Method for Perfluoroalkyltrifluoroborates and Perfluoroalkyldifluoroboranes", Z. Anorg. Allg. Chem., vol. 627 (2001) pp. 15-16.

Z.B. Zhou et al., "Novel Electrolyte Salts Based on Perfluoroalkyltrifuoroborate Anions 1. Synthesis and Characterization", Journal of Fluorine Chemistry, vol. 123 (2003) pp. 127-131.

* cited by examiner

ELECTROLYTE FORMULATIONS

The present invention relates to electrolyte formulations comprising at least one compound of formula (I) with perfluoroalkylcyanofluoroborate anions or perfluoroalkyltricyanoborate anions, ((per)fluoro)phenylcyanofluoroborate anions or ((per)fluoro)phenyltricyanoborate anions or phenylcyanofluoroborate anions which are monosubstituted or disubstituted with perfluoroalkyl groups having 1 to 4 C atoms or phenyltricyanoborate anions which are monosubstituted or disubstituted with perfluoroalkyl groups having 1 to 4 C atoms and their use in an electrochemical and/or optoelectronic device such as a photovoltaic cell, a capacitor, a light emitting device, an electrochromic or photo-electrochromic device, an electrochemical sensor and/or biosensor, preferably their use in a dye or quantum dot sensitized solar cell.

Electrolyte formulations form a crucial part of electrochemical and/or optoelectronic devices and the performance of the device largely depends on the physical and chemical properties of the various components of these electrolytes.

The term electrolytes is used herein in the sense of electrolyte formulation as defined below and will be used equally to electrolyte formulation within the disclosure.

Factors which are still impeding the technical application of many electrochemical and/or optoelectronic devices and in particular of dye or quantum dot sensitized solar cells, are reliability problems caused by the volatility of organic solvents based electrolytes. It is very difficult to maintain a tight sealing of the electrolyte in e.g. a DSC panel, which has to withstand the temperature differences of daily day-night cycles and the concomitant thermal expansion of the electrolyte. The abbreviation DSC means dye sensitized solar cell. This problem can be solved in principle by the use of ionic liquid-based electrolytes. For review "Ionic liquid electrolytes for dye-sensitized solar cells" see: M. Gorlov and L. Kloo, *Dalton Trans.*, 2008, p. 2655-2666.

Ionic liquids or liquid salts are typically ionic species which consist of an organic cation and a generally inorganic anion usually having melting points below 373 K. Various binary ionic liquid electrolytes have recently been applied to dye-sensitized solar cells. WO 2007/093961 and WO 2009/083901 describe so far the best power conversion efficiencies in ionic liquid-based electrolytes for DSC containing a significant quantity of organic salts with tetracyanoborate (TCB) anions.

However, there continues to be a demand for new and improved electrolytes based on ionic liquids with improved DSC efficiency over a broad temperature range including temperatures below room temperature and well above the temperature at which liquid freezing and precipitation may take place (i.e. in the range of 0° C. to 20° C.).

The object of the invention is therefore to provide electrolyte formulations for electrochemical and/or optoelectronic devices with equal or increased power conversion efficiency such as a photovoltaic cell, a capacitor, a light emitting device, an electrochromic or photo-electrochromic device, an electrochemical sensor and/or biosensor, especially for dye or quantum dot sensitized solar cells, especially preferably for dye sensitized solar cells over a broad temperature range, particularly additionally at low temperature. Low temperature is defined as the temperature range between 0° C. and 20° C.

Surprisingly it was found that electrolyte formulations comprising compounds of formula (I) as described below, e.g. perfluoroalkylcyanofluoroborate anions or perfluoroalkyltricyanoborate anions, fulfill such demands.

It is believed that formulations comprising perfluoroalkylcyanofluoroborate anions or perfluoroalkyltricyanoborate anions reduce the resistances owing to the charge transfer of and to the Nernst diffusion of redox-couple species (e.g. I$^-$ and I$_3^-$) at low temperatures as defined above.

The present invention therefore relates firstly to an electrolyte formulation comprising at least one compound of formula (I)

$$M^{a+}[B(R_f)(CN)_x(F)_y]_a^-  \quad (I)$$

in which M$^{a+}$ is an inorganic or organic cation,
R$_f$ denotes straight-chain or branched perfluoroalkyl groups having 1 to 4 C atoms, C$_6$F$_5$, C$_6$H$_5$, partially fluorinated phenyl or phenyl which is monosubstituted or disubstituted by perfluoroalkyl groups having 1 to 4 C atoms,
a is 1, 2, 3 or 4, x is 1, 2 or 3, y is 0, 1 or 2 and x+y is 3.

Compounds with [B(R$_f$)$_{4-x-y}$(CN)$_x$(F)$_y$]$_a$ anions are described in WO 2006/045405, in which x denotes 1, 2 or 3, y denotes 0 or 1, x+y≤4, particularly potassium tris(trifluoromethyl)cyanoborate, guanidinium tris(trifluoromethyl)cyanoborate and tritylium tris(trifluoromethyl)cyanoborate. However, WO 2006/045405 does not describe an electrolyte formulation comprising compounds of formula (I) as described above, specific compounds of formula (I) and it does not disclose the specific utility of these compounds as components of an electrolyte formulation for the given electrochemical and/or electrooptical devices, especially for DSC.

A straight-chain or branched perfluoroalkyl group having 1 to 4 C atoms is, for example, trifluoromethyl, pentafluoroethyl, heptafluoropropyl, heptafluoroisopropyl, nonafluorobutyl, nonafluoro-sec.-butyl or nonafluoro-tert.-butyl.

A straight-chain or branched alkyl group having 1 to 4 C atoms is, for example, methyl, ethyl, propyl, isopropyl, n-butyl, sec.-butyl or tert.-butyl.

R$_f$ in in formula (I) is in particular a straight-chain or branched perfluoroalkyl group having 1 to 4 C atoms or C$_6$F$_5$, particularly preferably trifluoromethyl, pentafluoroethyl, heptafluoropropyl or pentafluorophenyl, very particularly preferably trifluoromethyl or pentafluoroethyl.

In one embodiment, the invention relates to electrolyte formulations comprising at least one compound of formula (I) as described above in which x is 1 and y is 2, which relate to the anion [B(R$_f$)(CN)(F)$_2$], in which R$_f$ has a meaning or preferred meaning as described above.

In another embodiment, the invention relates to electrolyte formulations comprising at least one compound of formula (I) as described above in which x is 2 and y is 1, which relate to the anion [B(R$_f$)(CN)$_2$(F)], in which R$_f$ has a meaning or preferred meaning as described above.

In another embodiment, the invention relates to electrolyte formulations comprising at least one compound of formula (I) as described above in which x is 3 and y is 0, which relate to the anion [B(R$_f$)(CN)$_3$], in which R$_f$ has a meaning or preferred meaning as described above.

The comparative data as shown below document that electrolyte formulations containing these anions, preferably the anions [B(R$_f$)(CN)(F)$_2$] and [B(R$_f$)(CN)$_2$(F)], in which R$_f$ has a meaning or preferred meaning as described above, show a better overall performance in dye sensitized solar cells compared to electrolyte formulations containing tetracyanoborate as anion with the condition that the same cation is used.

There are no restrictions per se regarding the choice of cation of the compound of formula (I) in accordance with the present invention. Thus, M$^{a+}$ can be an inorganic or organic cation. However—for application in electrooptical devices such as dye-sensitized solar cells, M$^{a+}$ is preferably an organic cation selected from the group comprising sulfonium, oxonium, ammonium, phosphonium, uronium, thiouronium, guanidinium cations or heterocyclic cations, particularly preferably selected from the cations of formulae (1) to (8). The value a has to be adapted accordingly. Examples of organic cations are also polyammonium ions having a degree of charging z=4 or tritylium cation in which the phenyl groups may be substituted by straight-chain or branched alkyl groups having 1 to 20 C atoms, straight-chain or branched alkenyl having 2 to 20 C atoms and one or more double bonds or straight-chain or branched alkynyl having 2 to 20 C atoms and one or more triple bonds.

For the application in other electrochemical devices such as capacitors or lithium ion cells, $Ma^+$ is preferably a metal cation.

The metal cation may comprise metals from groups 1 to 12 of the Periodic Table.

Preferred metal cations are alkali metal cations, such as $Li^+$, $Na^+$, $K^+$, $Rb^+$, $Cs^+$, $Ag^+$, $Mg^{2+}$, $Cu^+$, $Cu^{2+}$, $Zn^{2+}$, $Ca^{2+}$, $Y^{+3}$, $Yb^{+3}$, $La^{+3}$, $Sc^{+3}$, $Ce^{+3}$, $Ce^{+4}$, $Nd^{+3}$, $Tb^{+3}$, $Sm^{+3}$ or complex (ligands containing) metal cations which include rare-earths, transitions or noble metals like Rhodium, Ruthenium, Iridium, Palladium, Platinum, Osmium, Cobalt, Nickel, Iron, Chromium, Molybdenium, Tungsten, Vanadium, Titanium, Zirconium, Hafnium, Thorium, Uranium or Gold.

Sulfonium cations can be described, for example by the formula (1) and oxonium cations can be described, for example, by the formula (2)

$$[(R^\circ)_3S]^+ \quad (1)$$

$$[(R^\circ)_3O]^+ \quad (2),$$

where $R^\circ$ denotes straight-chain or branched alkyl groups having 1-8 C atoms, $R'''_2N-$ or nonsubstituted phenyl or phenyl which is substituted by $R'''$, $OR'''$, $N(R''')_2$, CN or halogen and $R'''$ is independently of each other H or straight-chain or branched $C_1$ to $C_8$ alkyl.

$R^\circ$ of the $[(R^\circ)_3O]^+$ cation or $[(R^\circ)_3S]^+$ cation is preferably straight-chain alkyl having 1-8 C atoms or nonsubstituted phenyl or phenyl which is substituted by $R'''$, $OR'''$, $N(R''')_2$, CN or halogen and $R'''$ is independently of each other H or straight-chain or branched $C_1$ to $C_8$ alkyl, particularly preferably straight-chain alkyl having 1-8 C atoms, in particular methyl or ethyl, very particularly preferably ethyl. A particularly preferred sulfonium cation is diethyl-methylsulfonium.

Ammonium cations can be described, for example, by the formula (3)

$$[NR_4]^+ \quad (3),$$

where
R in each case, independently of one another, denotes H, $OR'$, $NR'_2$, with the proviso that a maximum of one substituent R in formula (3) is $OR'$, $NR'_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms,
which may be substituted by alkyl groups having 1-6 C atoms, where one or more R may be partially or fully substituted by halogens, in particular —F and/or —Cl, or partially by —OH, —OR', —NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', —NO$_2$ and where one or two non-adjacent carbon atoms in R which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R' may be =H, non-, partially or perfluorinated $C_1$- to $C_{18}$-alkyl, $C_3$- to $C_7$-cycloalkyl, nonsubstituted or substituted phenyl and X may be =halogen.

Phosphonium cations can be described, for example, by the formula (4)

$$[PR^2_4]^+ \quad (4),$$

where
$R^2$ in each case, independently of one another, denotes H, $OR'$ or $NR'_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms,
which may be substituted by alkyl groups having 1-6 C atoms, where one or more $R^2$ may be partially or fully substituted by halogens, in particular —F and/or —Cl, or partially by —OH, —OR', —NR'$_2$, —CN, —O(O)OH, —C(O)NR'$_2$, —SO$_2$NR'$_2$, —C(O)X, —SO$_2$OH, —SO$_2$X, —SR', —S(O)R', —SO$_2$R', —NO$_2$ and where one or two non-adjacent carbon atoms in $R^2$ which are not in the α-position may be replaced by atoms and/or atom groups selected from the group —O—, —S—, —S(O)—, —SO$_2$—, —SO$_2$O—, —O(O)—, —C(O)O—, —N$^+$R'$_2$—, —P(O)R'O—, —O(O)NR'—, —SO$_2$NR'—, —OP(O)R'O—, —P(O)(NR'$_2$)NR'—, —PR'$_2$=N— or —P(O)R'— where R'=H, non-, partially or perfluorinated $C_1$- to $C_{18}$-alkyl, $C_3$- to $C_7$-cycloalkyl, nonsubstituted or substituted phenyl and X=halogen.

However, cations of the formulae (3) and (4) in which all four or three substituents R and $R^2$ are fully substituted by halogens are excluded, for example the tris(trifluoromethyl)methylammonium cation, the tetrakis(trifluoromethyl)ammonium cation or the tetrakis(nonafluorobutyl)ammonium cation.

Uronium cations can be described, for example, by the formula (5)

$$[C(NR^3R^4)(OR^5)(NR^6R^7)]^+ \quad (5),$$

and thiouronium cations by the formula (6)

$$[C(NR^3R^4)(SR^5)(NR^6R^7)]^+ \quad (6),$$

where
$R^3$ to $R^7$ each, independently of one another, denote
H, where H is excluded for $R^5$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms,
which may be substituted by alkyl groups having 1-6 C atoms, where one or more of the substituents $R^3$ to $R^7$ may be partially or fully substituted by halogens, in particular —F and/or —Cl, or partially by —OH, —OR', —NR'$_2$, —CN, —O(O)OH, —C(O)NR'$_2$, —SO$_2$NR'$_2$, —C(O)X, —SO$_2$OH, —SO$_2$X, —SR', —S(O)R', —SO$_2$R', —NO$_2$ and where one or two non-adjacent carbon atoms in $R^3$ to $R^7$ which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R'=H, non-, partially or perfluorinated C$_1$- to C$_{18}$-alkyl, C$_3$- to C$_7$-cycloalkyl, nonsubstituted or substituted phenyl and X=halogen.

Guanidinium cations can be described by the formula (7)

[C(NR$^8$R$^9$)(NR$^{10}$R$^{11}$)(NR$^{12}$R$^{13}$)]$^+$  (7), where

R$^8$ to R$^{13}$ each, independently of one another, denote

H, —CN, NR'$_2$, —OR', straight-chain or branched alkyl having 1 to 20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one or more of the substituents R$^8$ to R$^{13}$ may be partially or fully substituted by halogens, in particular —F and/or —Cl, or partially by —OH, —OR', —NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', —NO$_2$ and where one or two non-adjacent carbon atoms in R$^8$ to R$^{13}$ which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R'=H, non-, partially or perfluorinated C$_1$- to C$_{18}$-alkyl, C$_3$- to C$_7$-cycloalkyl, nonsubstituted or substituted phenyl and X=halogen.

Heterocyclic cations can be described, for example by the formula (8)

[HetN]$^{z+}$  (8)

where

HetN$^{z+}$ denotes a heterocyclic cation selected from the group imidazolium, 1H-pyrazolium

3H-pyrazolium, 4H-pyrazolium

1-pyrazolinium, 2-pyrazolinium

3-pyrazolinium, 2,3-dihydroimidazolinium

4,5-dihydroimidazolinium, 2,5-dihydroimidazolinium pyrrolidinium, 1,2,4-triazolium

1,2,4-triazolium, 1,2,3-triazolium

1,2,3-triazolium, pyridinium pyridazinium, pyrimidinium piperidinium, morpholinium piperazinium piperazinium pyrazinium thiazolium oxazolium indolium quinolinium isoquinolinium quinoxalinium or indolinium where the substituents
$R^{1'}$ to $R^{4'}$ each, independently of one another, denote
H with the assumption that $R^{1'}$ and $R^{4'}$ are not simultaneously H,
straight-chain or branched alkyl having 1 to 20 C atoms, which optionally may be fluorinated or perfluorinated,
straight-chain or branched alkenyl having 2 to 20 C atoms and one or more double bonds, which optionally may be fluorinated or perfluorinated,
straight-chain or branched alkynyl having 2 to 20 C atoms and one or more triple bonds which optionally may be fluorinated or perfluorinated or
straight-chain or branched alkoxyalkyl having 2 to 8 C atoms.

A straight-chain or branched alkyl having 1-20 C atoms denotes an alkyl group having 1, 2, 3, 4, 5, 6, 7, 8, 9, 10, 11, 12, 13, 14, 15, 16, 17, 18, 19 or 20 C atoms, for example methyl, ethyl, isopropyl, n-propyl, isobutyl, n-butyl, tert-butyl, n-pentyl, 1-, 2- or 3-methylbutyl, 1,1-, 1,2- or 2,2-dimethylpropyl, 1-ethylpropyl, n-hexyl, n-heptyl, n-octyl, ethylhexyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or eicosyl, which optionally may be fluorinated or perfluorinated. The term "perfluorinated" means that all H atoms are substituted by F atoms in the given alkyl group. The term "fluorinated" means that at least one H atom of the given alkyl group is substituted by an F atom.

A straight-chain or branched alkenyl having 2 to 20 C atoms, in which a plurality of double bonds may also be present, is, for example, allyl, 2- or 3-butenyl, isobutenyl, sec-butenyl, furthermore 4-pentenyl, isopentenyl, hexenyl, heptenyl, octenyl, —$C_9H_{17}$, —$C_{10}H_{19}$ to —$C_{20}H_{39}$, preferably allyl, 2- or 3-butenyl, isobutenyl, sec-butenyl, furthermore preferably 4-pentenyl, isopentenyl or hexenyl, which optionally may be fluorinated or perfluorinated.

A straight-chain or branched alkynyl having 2 to 20 C atoms, in which a plurality of triple bonds may also be present, is, for example, ethynyl, 1- or 2-propynyl, 2- or 3-butynyl, furthermore 4-pentynyl, 3-pentynyl, hexynyl, hept-ynyl, octynyl, —$C_9H_{15}$, —$C_{10}H_{17}$ to —$C_{20}H_{37}$, preferably ethynyl, 1- or 2-propynyl, 2- or 3-butynyl, 4-pentynyl, 3-pentynyl or hexynyl, which optionally may be fluorinated or perfluorinated.

A straight-chain or branched alkoxyalkyl having 2 to 12 C atoms is, for example, methoxymethyl, 1-methoxyethyl, 1-methoxypropyl, 1-methoxy-2-methyl-ethyl, 2-methoxypropyl, 2-methoxy-2-methyl-propyl, 1-methoxybutyl, 1-methoxy-2,2-dimethyl-ethyl, 1-methoxy-pentyl, 1-methoxyhexyl, 1-methoxy-heptyl, ethoxymethyl, 1-ethoxyethyl, 1-ethoxypropyl, 1-ethoxy-2-methyl-ethyl, 1-ethoxybutyl, 1-ethoxy-2,2-dimethyl-ethyl, 1-ethoxypentyl, 1-ethoxyhexyl, 1-ethoxyheptyl, propoxymethyl, 1-propoxyethyl, 1-propoxypropyl, 1-propoxy-2-methyl-ethyl, 1-propoxybutyl, 1-propoxy-2,2-dimethyl-ethyl, 1-propoxypentyl, butoxymethyl, 1-butoxyethyl, 1-butoxypropyl or 1-butoxybutyl. Particularly preferred is methoxymethyl, 1-methoxyethyl, 2-methoxy-propyl, 1-methoxypropyl, 2-methoxy-2-methyl-propyl or 1-methoxybutyl.

Nonsubstituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, each of which may be substituted by $C_1$- to $C_6$-alkyl groups, where the cycloalkyl group or the cycloalkyl group substituted by $C_1$- to $C_6$-alkyl groups may in turn also be substituted by halogen atoms, such as F, Cl, Br or I, in particular F or Cl, or by —OH, —OR', —NR', —CN, —C(O)OH, —C(O)NR'$_2$, —SO$_2$NR'$_2$, —C(O)X, —SO$_2$OH, —SO$_2$X, —SR', —S(O)R', —SO$_2$R', —NO$_2$.

In the substituents R, $R^2$ to $R^{13}$, one or two non-adjacent carbon atoms which are not bonded in the α-position to the heteroatom may also be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'—, where R'=non-, partially or perfluorinated $C_1$- to $C_{18}$-alkyl, $C_3$- to $C_7$-cycloalkyl, nonsubstituted or substituted phenyl.

Without restricting generality, examples of substituents R, $R^2$ to $R^{13}$ modified in this way are:

—OCH$_3$, —OCH(CH$_3$)$_2$, —CH$_2$OCH$_3$, —CH$_2$—CH$_2$—O—CH$_3$, —C$_2$H$_4$OCH(CH$_3$)$_2$, —C$_2$H$_4$C$_2$H$_5$, —C$_2$H$_4$SCH(CH$_3$)$_2$, —S(O)CH$_3$, —SO$_2$CH$_3$, —SO$_2$C$_6$H$_5$, —SO$_2$C$_3$H$_7$, —SO$_2$CH(CH$_3$)$_2$, —SO$_2$CH$_2$CF$_3$, —CH$_2$SO$_2$CH$_3$, —O—C$_4$H$_8$—O—C$_4$H$_9$, —CF$_3$, —C$_2$F$_5$, —C$_3$F$_7$, —C$_4$F$_9$, —C(CF$_3$)$_3$, —CF$_2$SO$_2$CF$_3$, —C$_2$F$_4$N(C$_2$F$_5$)C$_2$F$_5$, —CHF$_2$, —CH$_2$CF$_3$, —C$_2$F$_2$H$_3$, —C$_3$FH$_6$, —CH$_2$C$_3$F$_7$, —C(CFH$_2$)$_3$, —CH$_2$C(O)OH, —CH$_2$C$_6$H$_5$, —C(O)C$_6$H$_5$ or P(O)(C$_2$H$_5$)$_2$.

In R', C$_3$- to C$_7$-cycloalkyl is, for example, cyclopropyl, cyclobutyl, cyclopentyl, cyclohexyl or cycloheptyl.

In R', substituted phenyl denotes phenyl which is substituted by C$_1$- to C$_6$-alkyl, C$_1$- to C$_6$-alkenyl, —CN, —NO$_2$, F, Cl, Br, I, —OH, —C$_1$-C$_6$-alkoxy, NR''$_2$, —COOH, —SO$_2$X', —SR'', —S(O)R'', —SO$_2$R'', SO$_2$NR''$_2$ or SO$_3$H, where X' denotes F, Cl or Br and R'' denotes a non-, partially or perfluorinated C$_1$- to C$_6$-alkyl or C$_3$- to C$_7$-cycloalkyl as defined for R', for example o-, m- or p-methylphenyl, o-, m- or p-ethylphenyl, o-, m- or p-propylphenyl, o-, m- or p-isopropylphenyl, o-, m- or p-tert-butylphenyl, o-, m- or p-nitrophenyl, o-, m- or p-hydroxyphenyl, o-, m- or p-methoxyphenyl, o-, m- or p-ethoxy-phenyl, o-, m-, p-(trifluoromethyl)phenyl, o-, m-, p-(trifluoromethoxy)phenyl, o-, m-, p-(trifluoromethylsulfonyl)phenyl, o-, m- or p-fluorophenyl, o-, m- or p-chlorophenyl, o-, m- or p-bromophenyl, o-, m- or p-iodophenyl, further preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluoro-phenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethyl-phenyl.

In accordance with the invention, suitable substituents R and $R^2$ to $R^{13}$ of the compounds of the formulae (3) to (7), besides H, are preferably: C$_1$- to C$_{20}$-, in particular C$_1$- to C$_{14}$-alkyl groups, and saturated or unsaturated, i.e. also aromatic, C$_3$- to C$_7$-cycloalkyl groups, which may be substituted by C$_1$- to C$_6$-alkyl groups, in particular phenyl.

The substituents R and $R^2$ in the compounds of the formula (3) or (4) may be identical or different. Preferably, three or four substituents R in formula (3) are identical. Preferably, three or four substitutents $R^2$ in formula (4) are identical.

The substituents R and $R^2$ are particularly preferably methyl, ethyl, isopropyl, propyl, butyl, sec-butyl, pentyl, hexyl, octyl, decyl or tetradecyl.

Up to four substituents of the guanidinium cation $[C(NR^8R^9)(NR^{10}R^{11})(NR^{12}R^{13})]^+$ may also be bonded in pairs in such a way that mono-, bi- or polycyclic cations are formed.

Without restricting generality, examples of such guanidinium cations are:

where the substituents $R^8$ to $R^{10}$ and $R^{13}$ can have a meaning or particularly preferred meaning indicated above.

If desired, the carbocycles or heterocycles of the guanidinium cations indicated above may also be substituted by C$_1$- to C$_6$-alkyl, C$_1$-to C$_6$-alkenyl, —CN, —NO$_2$, F, Cl, Br, I, —OH, —C$_1$-C$_6$-alkoxy, —NR'$_2$, —SR', —S(O)R', —SO$_2$R', —COOH, —SO$_2$NR'$_2$, —SO$_2$X' or —SO$_3$H, where X and R' have a meaning indicated above, substituted or nonsubstituted phenyl or an nonsubstituted or substituted heterocycle.

Up to four substituents of the uronium cation $[C(NR^3R^4)(OR^5)(NR^6R^7)]^+$ or thiouronium cation $[C(NR^3R^4)(SR^5)(NR^6R^7)]^+$ may also be bonded in pairs in such a way that mono-, bi- or polycyclic cations are formed.

Without restricting generality, examples of such cations are indicated below, where Y=O or S:

-continued where the substituents $R^3$, $R^5$ and $R^6$ can have a meaning or particularly preferred meaning indicated above.

If desired, the carbocycles or heterocycles of the cations indicated above may also be substituted by $C_1$- to $C_6$-alkyl, $C_1$- to $C_6$-alkenyl, —CN, —NO$_2$, F, Cl, Br, I, —OH, —$C_1$-$C_6$-alkoxy, —NR'$_2$, —SR', —S(O)R', —SO$_2$R', —COOH, SO$_2$NR'$_2$, SO$_2$X or SO$_3$H or substituted or nonsubstituted phenyl or an nonsubstituted or substituted heterocycle, where X and R' have a meaning indicated above.

The substituents $R^3$ to $R^{13}$ are each, independently of one another, preferably a straight-chain or branched alkyl group having 1 to 16 C atoms. The substituents $R^3$ and $R^4$, $R^6$ and $R^7$, $R^8$ and $R^9$, $R^{10}$ and $R^{11}$ and $R^{12}$ and $R^{13}$ in compounds of the formulae (5) to (7) may be identical or different. $R^3$ to $R^{13}$ are particularly preferably each, independently of one another, methyl, ethyl, n-propyl, isopropyl, n-butyl, tert-butyl, sec-butyl, phenyl, hexyl or cyclohexyl, very particularly preferably methyl, ethyl, n-propyl, isopropyl, n-butyl or hexyl.

In accordance with the invention, suitable substituents $R^{1'}$ and $R^{4'}$ of compounds of the formula (8), are independently of each other preferably: $C_1$- to $C_{20}$—, in particular $C_1$- to $C_6$-alkyl groups.

In accordance with the invention, suitable substituents $R^{2'}$ and $R^{3'}$ of compounds of the formula (8), are independently of each other preferably: H, $C_1$- to $C_{20}$-, in particular H or $C_1$- to $C_6$-alkyl groups.

HetN$^{z+}$ is preferably imidazolium    pyridinium pyrrolidinium   pyrazolium or pyrimidinium   piperidinium indolinium where the substituents $R^{1'}$ to $R^{4'}$ each, independently of one another, have a meaning described above or below.

HetN$^{z+}$ is particularly preferably or imidazolium    pyrrolidinium where the substituents $R^{1'}$ to $R^{4'}$ each, independently of one another, have a meaning described above or below.

The substituents $R^{1'}$ and $R^{4'}$ are each, independently of one another, particularly preferably methyl, ethyl, isopropyl, propyl, butyl, sec-butyl, tert-butyl, n-pentyl or n-hexyl. They are very particularly preferably methyl, ethyl, n-butyl or n-hexyl. In pyrrolidinium or imidazolium, the two substituents $R^{1'}$ and $R^{4'}$ are preferably different.

The substituents $R^{2'}$ and $R^{3'}$ are in each case, independently of one another, in particular H, methyl, ethyl, isopropyl, propyl, butyl, sec-butyl or tert-butyl. $R^{2'}$ in 2-position of the imidazolium ring is particularly preferably H, methyl, ethyl, isopropyl, propyl or n-butyl, particularly preferably H or methyl. $R^{2'}$ in 4- and 5-position of the imidazolium ring is preferably H. The substituents $R^{2'}$ and $R^{3'}$ of the pyrrolidinium ring are preferably H.

Preferred 1,1-dialkylpyrrolidinium cations are, for example, 1,1-dimethyl-pyrrolidinium, 1-methyl-1-ethylpyrrolidinium, 1-methyl-1-propylpyrrolidinium, 1-methyl-1-butylpyrrolidinium, 1-methyl-1-pentylpyrrolidinium, 1-methyl-1-hexylpyrrolidinium, 1-methyl-1-heptylpyrrolidinium, 1-methyl-1-octylpyrrolidinium, 1-methyl-1-nonylpyrrolidinium, 1-methyl-1-decylpyrrolidinium, 1,1-diethylpyrrolidinium, 1-ethyl-1-propylpyrrolidinium, 1-ethyl-1-butylpyrrolidinium, 1-ethyl-1-pentylpyrrolidinium, 1-ethyl-1-hexylpyrrolidinium, 1-ethyl-1-heptylpyrrolidinium, 1-ethyl-1-octylpyrrolidinium, 1-ethyl-1-nonylpyrrolidinium, 1-ethyl-1-decylpyrrolidinium, 1,1-dipropylpyrrolidinium, 1-propyl-1-methylpyrrolidinium, 1-propyl-1-butylpyrrolidinium, 1-propyl-1-pentylpyrrolidinium, 1-propyl-1-hexylpyrrolidinium, 1-propyl-1-heptylpyrrolidinium, 1-propyl-1-octylpyrrolidinium, 1-propyl-1-nonylpyrrolidinium, 1-propyl-1-decylpyrrolidinium, 1,1-dibutylpyrrolidinium, 1-butyl-1-methylpyrrolidinium, 1-butyl-1-pentylpyrrolidinium, 1-butyl-1-hexylpyrrolidinium, 1-butyl-1-heptylpyrrolidinium, 1-butyl-1-octylpyrrolidinium, 1-butyl-1-nonylpyrrolidinium, 1-butyl-1-decylpyrrolidinium, 1,1-dipentylpyrrolidinium, 1-pentyl-1-hexylpyrrolidinium, 1-pentyl-1-heptylpyrrolidinium, 1-pentyl-1-octylpyrrolidinium, 1-pentyl-1-nonylpyrrolidinium, 1-pentyl-1-decylpyrrolidinium, 1,1-dihexyl-pyrrolidinium, 1-hexyl-1-heptylpyrrolidinium, 1-hexyl-1-octylpyrrolidinium, 1-hexyl-1-nonylpyrrolidinium, 1-hexyl-1-decylpyrrolidinium, 1,1-dihexyl-pyrrolidinium, 1-hexyl-1-heptylpyrrolidinium, 1-hexyl-1-octylpyrrolidinium, 1-hexyl-1-nonylpyrrolidinium, 1-hexyl-1-decylpyrrolidinium, 1,1-diheptyl-pyrrolidinium, 1-heptyl-1-octylpyrrolidinium, 1-heptyl-1-nonylpyrrolidinium, 1-heptyl-1-decylpyrrolidinium, 1,1-dioctylpyrrolidinium, 1-octyl-1-nonylpyrrolidinium, 1-octyl-1-decylpyrrolidinium, 1,1-dinonylpyrrolidinium, 1-nonyl-1-decylpyrrolidinium or 1,1-didecylpyrrolidinium. Very particular preference is given to 1-butyl-1-methylpyrrolidinium or 1-propyl-1-methylpyrrolidinium.

Preferred 1-alkyl-1-alkoxyalkylpyrrolidinium cations are, for example, 1-(2-methoxyethyl)-1-methylpyrrolidinium, 1-(2-methoxyethyl)-1-ethylpyrrolidinium, 1-(2-methoxyethyl)-1-propylpyrrolidinium, 1-(2-methoxyethyl)-1-butylpyrrolidinium, 1-(2-ethoxyethyl)-1-methylpyrrolidinium, 1-ethoxymethyl-1-methylpyrrolidinium. Very particular preference is given to 1-(2-methoxyethyl)-1-methylpyrrolidinium.

Preferred 1,3-dialkylimidazolium cations are, for example, 1-ethyl-3-methyl-imidazolium, 1-methyl-3-propylimidazolium, 1-methyl-2,3-dimethylimidazolium, 1-ethyl-2,3-dimethylimidazolium, 1-propyl-2,3-dimethylimidazolium, 1-butyl-2,3-dimethylimidazolium, 1-butyl-3-methylimidazolium, 1-methyl-3-pentylimidazolium, 1-ethyl-3-propylimidazolium, 1-butyl-3-ethylimidazolium, 1-ethyl-3-pentylimidazolium, 1-butyl-3-propylimidazolium, 1,3-dimethylimidazolium, 1,3-diethylimidazolium, 1,3-dipropylimidazolium, 1,3-dibutylimidazolium, 1,3-dipentylimidazolium, 1,3-dihexylimidazolium, 1,3-diheptylimidazolium, 1,3-dioctylimidazolium, 1,3-dinonylimidazolium, 1,3-didecylimidazolium, 1-hexyl-3-methylimidazolium, 1-heptyl-3-methylimidazolium, 1-methyl-3-octylimidazolium, 1-methyl-3-nonylimidazolium, 1-decyl-3-methylimidazolium, 1-ethyl-3-hexyl-imidazolium, 1-ethyl-3-heptylimidazolium, 1-ethyl-3-octylimidazolium, 1-ethyl-3-nonylimidazolium or 1-decyl-3-ethylimidazolium. Particularly preferred cations are 1-ethyl-3-methylimidazolium, 1-butyl-3-methyl-imidazolium or 1-methyl-3-propylimidazolium.

Preferred 1-alkoxyalkyl-3-alkylimidazolium cations are, for example 1-(2-methoxyethyl)-3-methylimidazolium, 1-(2-methoxyethyl)-3-ethylimidazolium, 1-(2-methoxyethyl)-3-propylimidazolium, 1-(2-methoxyethyl)-3-butylimidazolium, 1-(2-ethoxyethyl)-3-methylimidazolium, 1-ethoxymethyl-3-methylimidazolium.

Preferred 1-alkenyl-3-alkylimidazolium cations are, for example 1-allyl-3-methyl-imidazolium or 1-allyl-2,3-dimethylimidazolium.

In chemistry, an electrolyte is any substance containing free ions that make the substance electrically conductive. The most typical electrolyte is an ionic solution, but molten electrolytes and solid electrolytes are also possible.

An electrolyte formulation according to the invention is therefore an electrically conductive medium, basically due to the presence of at least one substance that is present in a dissolved and or in molten state i.e. supporting an electric conductivity via motion of ionic species.

Preferably, the electrolyte formulation according to the invention comprise at least one compound of formula (I) in which $M^{a+}$ is a cation selected from cations of formulae (1), (3), (4), (6) or (8) as defined or particularly preferably described.

Particularly preferably, the electrolyte formulation according to the invention comprises at least one compound of formula (I) in which $M^{a+}$ is a cation selected from cations of formula (1) or (8) as defined or particularly preferably described.

Very particularly preferably, the electrolyte formulation according to the invention comprises at least one compound of formula (I) in which $M^{a+}$ is a cation selected from cations of formula (I) as defined or particularly preferably described.

Very particularly preferably, the electrolyte formulation according to the invention comprises at least one compound of formula (I) in which $M^{a+}$ is a cation selected from cations of formula (8) as defined or particularly preferably described.

The present invention relates therefore very particularly preferably to an electrolyte formulation comprising at least one compound of formula (I) as described above in which $M^{a+}$ of the compound of formula (I) is imidazolium            pyrrolidinium where the substituents $R^{1'}$ to $R^{4'}$ each, independently of one another, have a meaning as described above or below preferably or as preferably described or in which $M^{a+}$ has the meaning of 1,1-dialkylpyrrolidinium, 1-alkyl-1-alkoxyalkylpyrrolidinium, 1,3-dialkylimidazolium, 1-alkenyl-3-alkylimidazolium or 1-alkoxyalkyl-3-alkylimidazolium as described above.

Especially very particularly preferably, the electrolyte formulation according to the invention comprise at least one compound of formula (I) in which $Ma^+$ is imidazolium where the substituents $R^{1'}$ to $R^{4'}$ each, independently of one another, have a meaning as described above or below or as preferably described or in which Ma⁺ has the meaning of 1,3-dialkylimidazolium, 1-alkenyl-3-alkylimidazolium or 1-alkoxyalkyl-3-alkylimidazolium as described above.

Typical molar concentrations of the compound of formula (I) as described above in the electrolyte formulations range from 0.1 to 5.5 M, preferably from 0.8 to 3 M. This molar concentration in the electrolyte may be achieved with one or more compounds of formula (I) having an organic cation or with mixtures comprising at least one compound of formula (I) having an organic cation and at least one compound of formula (I) having an inorganic cation.

Preferred inorganic salts of formula (I) are compounds of formula (I) in which the cation is a metal cation such as lithium, sodium, potassium, silver, magnesium, calcium or zinc.

For the purpose of the present invention, the molar concentration refer to the concentration at 25° C.

Other components of the electrolyte formulation are one or several further salts, solvents, iodine and others, as indicated further below.

If the electrolyte formulation is a binary system, it comprises two salts, one further salt and a compound of formula (I) as described above. If the electrolyte formulation is a ternary system, it comprises two further salts and a compound of formula (I) as described above. The binary system comprises 90-20 weight %, preferably 80-55 weight %, more preferably 70-60 weight % of the further salt and 10-80 weight %, preferably 20-45 weight % or more preferably 30-40 weight % of the compound of formula (I) as described above. The percentages in this paragraph are expressed with respect to the total of salts (=100 weight %) present in the electrolyte formulation according to the invention. Amounts of further, generally optional components (additives) indicated below, such as N-containing compounds having unshared electron pairs, iodine, solvents, polymers, and nanoparticles, for example, are not considered therein. The same percentages apply to ternary or quaternary systems which means the total of the further salts has to be used in the given ranges, e.g. two further ionic liquids are comprised in e.g. 90-20 weight. % in the electrolyte formulation according to the invention.

According to another embodiment of the present invention, the electrolyte formulation comprises at least one further salt with organic cations as defined above as cations of formulae (1) to (8) and an anion selected from a halide ion, such as F⁻, Cl⁻, I⁻, a polyhalide ion, a fluoroalkanesulfonate, a fluoroalkanecarboxylate, a tri(fluoroalkylsulfonyl)methide, a bis(fluoroalkylsulfonyl)imide, a nitrate, a hexafluorophosphate, a tris-, bis- and mono-(fluoroalkyl)fluorophosphate, a tetrafluoroborate, a dicyanamide, a tricyanomethide, a tetracyanoborate, a thiocyanate, an alkylsulfonate or an alkylsulfate, with fluoroalkane having 1 to 20 C atoms, preferably perflu-orinated, fluoroalkyl having 1 to 20 C atoms and alkyl having 1 to 20 C atoms. Fluoroalkane or fluoroalkyl is preferably perfluorinated.

Preferably, the further salts are selected from salts comprising anions such as iodide, thiocyanate or tetracyanoborate, particularly preferred further salts are iodides.

However, to limit the amount of different cations in the electrolyte formulations, especially for DSC, the organic cations may be selected from the definitions for the cations of the compounds of formula (I). Therefore, according to another preferred embodiment of the present invention, the electrolyte formulation comprises at least one compound of formula (I) as described above and at least one further iodide in which the organic cations as preferably described above.

Particularly preferred examples of the at least one further salt are 1-ethyl-3-methylimidazolium iodide, 1-propyl-3-methylimidazolium iodide, 1-butyl-3-methyl-imidazolium iodide, 1-hexyl-3-methylimidazolium iodide, 1,3-dimethyl-imidazolium iodide, 1-allyl-3-methylimidazolium iodide, N-butyl-N-methylpyrrolidinium iodide or N,N-dimethyl-pyrrolidinium iodide.

In another embodiment of the invention, guanidinium thiocyanate may be added to the electrolyte formulation according to the invention.

The electrolyte formulation of the invention preferably comprises iodine ($I_2$). Preferably, it comprises from 0.01 to 50 weight %, more preferably 0.1 to 20 weight % and most preferably from 1 to 10 weight % of $I_2$.

In a preferred embodiment, the electrolyte formulation of the present invention further comprises at least one compound containing a nitrogen atom having non-shared electron pairs. Examples of such compounds are found in EP 0 986 079 A2, starting on page 2, lines 40-55, and again from page 3, lines 14 extending to page 7, line 54, which are expressly incorporated herein by reference. Preferred examples of compounds having non-shared electron pairs include imidazole and its derivatives, particularly benzimidazole and its derivatives.

The electrolyte formulation of the present invention comprises less than 50% of an organic solvent. Preferably, the electrolyte formulation comprises less than 40%, more preferably less than 30%, still more preferably less than 20% and even less than 10%. Most preferably, the electrolyte formulation comprises less than 5% of an organic solvent. For example, it is substantially free of an organic solvent. Percentages are indicated on the basis of weight %.

Organic solvents, if present in such amounts as indicated above, may be selected from those disclosed in the literature. Preferably, the solvent, if present, has a boiling point higher than 160 degrees centigrade, more preferably higher than 190 degrees such as propylene carbonate, ethylene carbonate, N-methyloxazolidinone, N,N'-dimethylimidazolidinone, tetraglyme and methoxy-substituted nitriles or sulfones which are preferably asymmetrically substituted such as 2-ethanesulfonyl-propane, 1-ethanesulfonyl-2-methyl-propane or 2-(propane-2-sulfonyl)-butane.

If a solvent is present in the electrolyte formulation, there may further be comprised a polymer as gelling agent, wherein the polymer is polyvinylidenefluoride, polyvinylidene-hexafluoropropylene, polyvinylidene-hexafluoropropylene-chlorotrifluoroethylene copolymers, nafion, polyethylene oxide, polymethylmethacrylate, polyacrylonitrile, polypropylene, polystyrene, polybutadiene, polyethyleneglycol, polyvinylpyrrolidone, polyaniline, polypyrrole, polythiophene. The purpose of adding these polymers to electrolyte formulations is to make liquid electrolytes into quasi-solid or solid electrolytes, thus improving solvent retention, especially during aging.

The electrolyte formulation of the invention may further comprise metal oxide nanoparticles like $SiO_2$, $TiO_2$, $Al_2O_3$, MgO or ZnO, for example, which are also capable of increasing solidity and thus solvent retention.

The electrolyte formulation of the invention has many applications. For example, it may be used in an optoelectronic andor electrochemical device such as a photovoltaic cell, a capacitor, a light emitting device, an electrochromic or photo-electrochromic device, an electrochemical sensor and/or biosensor. Also the use in electrochemical batteries is possible, for example in a lithium ion battery or a double layer capacitor.

The present invention therefore relates further to the use of the electrolyte formulation as described in detail above in an electrochemical and/or optoelectronic device, preferred in a photovoltaic cell, a capacitor, a light emitting device, an electrochromic or photo-electrochromic device, an electrochemical sensor and/or biosensor. Preferably, the electrolyte formulation may be used in dye sensitized solar cells.

The present invention therefore relates furthermore to an electrochemical and/or optoelectronic device, preferably a photovoltaic cell, a capacitor, a light emitting device, an electrochromic or photo-electrochromic device, an electrochemical sensor and/or biosensor, comprising an electrolyte formulation comprising at least one compound of formula (I)

$$M^{a+}[B(R_f)(CN)_x(F)_y]_a^- \qquad (I)$$

in which $M^{a+}$ is an inorganic or organic cation,
$R_f$ denotes straight-chain or branched perfluoroalkyl groups having 1 to 4 C atoms, $C_6F_5$, $C_6H_5$, partially fluorinated phenyl or phenyl which is monosubstituted or disubstituted by perfluoroalkyl groups having 1 to 4 C atoms,
a is 1, 2, 3 or 4,
x is 1, 2 or 3,
y is 0, 1 or 2 and x+y is 3.

According to a preferred embodiment, the device of the present invention is a dye or quantum dot sensitized solar cell, particularly preferably a dye sensitized solar cell.

Quantum dot sensitized solar cells are disclosed in U.S. Pat. No. 6,861,722, for example. In dye-sensitized solar cells, a dye is used to absorb the sunlight to convert into the electrical energy. Examples of dyes are disclosed in EP 0 986 079 A2, EP 1 180 774 A2 or EP 1 507 307 A1.

Preferred dyes are Z907 or Z907Na which are both an amphiphilic ruthenium sensitizer.

In a preferred embodiment, the dye is coadsorbed with a phosphinic acid. A preferred example of a phosphinic acid is bis(3,3-dimethyl-butyl)-phosphinic acid (DINHOP) as disclosed in M. Wang et al, Dalton Trans., 2009, 10015-10020.

The dye Z907Na means NaRu(2,2'-bipyridine-4-carboxylic acid-4'-carboxylate)(4,4'-dinonyl-2,2'-bipyridine)(NCS)$_2$.

For example, a dye-sensitized solar cell comprises a photoelectrode, a counter electrode and, between the photoelectrode and the counterelectrode, an electrolyte formulation or a charge transporting material, and wherein a sensitizing dye is absorbed on the surface of the photoelectrode, on the side facing the counterelectrode.

According to a preferred embodiment of the device according to the invention, it comprises a semiconductor, the electrolyte formulation as described above and a counter electrode.

According to a preferred embodiment of the invention, the semiconductor is based on material selected from the group of Si, $TiO_2$, $SnO_2$, $Fe_2O_3$, $WO_3$, ZnO, $Nb_2O_5$, CdS, ZnS, PbS, $Bi_2S_3$, CdSe, GaP, InP, GaAs, CdTe, $CuInS_2$, and/or $CuInSe_2$. Preferably, the semiconductor comprises a mesoporous surface, thus increasing the surface optionally covered by a dye and being in contact with the electrolyte. Preferably, the semiconductor is present on a glass support or plastic or metal foil. Preferably, the support is conductive.

The device of the present invention preferably comprises a counter electrode. For example, fluorine doped tin oxide or tin doped indium oxide on glass (FTO- or ITO-glass, respectively) coated with Pt, carbon of preferably conductive allotropes, polyaniline or poly(3,4-ethylenedioxythiophene) (PEDOT). Metal substrates such as stainless steel or titanium sheet may be possible substrates beside glass.

The device of the present invention may be manufactured as the corresponding device of the prior art by simply replacing the electrolyte by the electrolyte formulation of the present invention. For example, in the case of dye-sensitized solar cells, device assembly is disclosed in numerous patent literature, for example WO 91/16719 (examples 34 and 35), but also scientific literature, for example in Barbé, C. J., Arendse, F., Comte, P., Jirousek, M., Lenzmann, F., Shklover, V., Grätzel, M. J. Am. Ceram. Soc. 1997, 80, 3157; and Wang, P., Zakeeruddin, S. M., Comte, P., Charvet, R., Humphry-Baker, R., Grätzel, M. J. Phys. Chem. B 2003, 107, 14336.

Preferably, the sensitized semiconducting material serves as a photoanode. Preferably, the counter electrode is a cathode.

The present invention provides a method for preparing a photoelectric cell comprising the step of bringing the electrolyte formulation of the invention in contact with a surface of a semiconductor, said surface optionally being coated with a sensitizer. Preferably, the semiconductor is selected from the materials given above, and the sensitizer is preferably selected from quantum dots and/or a dye as disclosed above, particularly preferably selected from a dye.

Preferably, the electrolyte formulation may simply be pured on the semiconductor. Preferably, it is applied to the otherwise completed device already comprising a counter electrode by creating a vacuum in the internal lumen of the cell through a hole in the counter electrode and adding the electrolyte formulation as disclosed in the reference of Wang et al., J. Phys. Chem. B 2003, 107, 14336.

The invention furthermore relates to compounds of formula (I-a)

$$M^{a+}[B(R_f)(CN)(F)_2]_a^- \qquad (I\text{-}a)$$

in which,
$M^{a+}$ is an organic cation selected from the group comprising sulfonium, oxonium, ammonium, phosphonium, uronium, thiouronium, guanidinium cations or heterocyclic cations as described above,
$R_f$ denotes straight-chain or branched perfluoroalkyl groups having 1 to 4 C atoms, $C_6F_5$, $C_6H_5$, partially fluorinated phenyl or phenyl which is monosubstituted or disubstituted by perfluoroalkyl groups having 1 to 4 C atoms, preferably denotes straight-chain or branched perfluoroalkyl groups having 1 to 4 C atoms or $C_6F_5$, and a denotes 1.

Specific examples of compounds of formula (I-a) are compounds selected from the group
1-ethyl-3-methylimidazolium [B($C_2F_5$)$CNF_2$],
1-ethyl-2,3-dimethylimidazolium [B($C_2F_5$)$CNF_2$],
1-(2-methoxyethyl)-3-methylimidazolium [B($C_2F_5$)$CNF_2$],
1-butyl-3-methylimidazolium [B($C_2F_5$)$CNF_2$],
1-butyl-1-methylpyrrolidinium [B($C_2F_5$)$CNF_2$],
tributyl-methylammonium [B($C_2F_5$)$CNF_2$],
tetra-n-butylammonium [B($C_2F_5$)$CNF_2$], tributyl-methylphosphonium [B(C$_2$F$_5$)CNF$_2$],
tetra-phenylphosphonium [B(C$_2$F$_5$)CNF$_2$],
diethyl-methylsulfonium [B(C$_2$F$_5$)CNF$_2$],
S-ethyl-N,N,N',N'-tetramethylisothiouronium [B(C$_2$F$_5$)CNF$_2$],
1-ethyl-3-methylimidazolium [B(CF$_3$)CNF$_2$],
1-ethyl-2,3-dimethylimidazolium [B(CF$_3$)CNF$_2$],
1-(2-methoxyethyl)-3-methylimidazolium [B(CF$_3$)CNF$_2$],
1-butyl-3-methylimidazolium [B(CF$_3$)CNF$_2$],
1-butyl-1-methylpyrrolidinium [B(CF$_3$)CNF$_2$],
tributyl-methylammonium [B(CF$_3$)CNF$_2$],
tetra-n-butylammonium [B(CF$_3$)CNF$_2$],
tributyl-methylphosphonium [B(CF$_3$)CNF$_2$],
tetra-phenylphosphonium [B(CF$_3$)CNF$_2$],
diethyl-methylsulfonium [B(CF$_3$)CNF$_2$],
ethyl-tetramethylisothiouronium [B(CF$_3$)CNF$_2$].

The invention furthermore relates to compounds of formula (I-b)

$$M^{a+}[B(R_f)(CN)_2(F)]_a^-  \quad (I\text{-}b)$$

in which,
$M^{a+}$ is an organic cation selected from the group comprising sulfonium, oxonium, ammonium, phosphonium, uronium, thiouronium, guanidinium cations or heterocyclic cations as described above
$R_f$ denotes straight-chain or branched perfluoroalkyl groups having 1 to 4 C atoms, C$_6$F$_5$, C$_6$H$_5$, partially fluorinated phenyl or phenyl which is monosubstituted or disubstituted by perfluoroalkyl groups having 1 to 4 C atoms, preferably denotes straight-chain or branched perfluoroalkyl groups having 1 to 4 C atoms or C$_6$F$_5$, and a denotes 1.

Specific examples of compounds of formula (I-b) are compounds selected from the group
1-ethyl-3-methylimidazolium [B(C$_2$F$_5$)(CN)$_2$F],
1-(2-methoxyethyl)-3-methylimidazolium [B(C$_2$F$_5$)(CN)$_2$F],
1-butyl-3-methylimidazolium [B(C$_2$F$_5$)(CN)$_2$F],
1-butyl-1-methylpyrrolidinium [B(C$_2$F$_5$)(CN)$_2$F],
tetra-phenylphosphonium [B(C$_2$F$_5$)(CN)$_2$F],
tetra-n-butylammonium [B(C$_2$F$_5$)(CN)$_2$F],
1-ethyl-3-methylimidazolium [B(CF$_3$)(CN)$_2$F],
1-(2-methoxyethyl)-3-methylimidazolium [B(CF$_3$)(CN)$_2$F],
tetra-phenylphosphonium [B(CF$_3$)(CN)$_2$F],
1-butyl-3-methylimidazolium [B(CF$_3$)(CN)$_2$F],
1-butyl-1-methylpyrrolidinium [B(CF$_3$)(CN)$_2$F],
1-ethyl-3-methylimidazolium [B(C$_2$F$_5$)CNF$_2$],
1-ethyl-2,3-dimethylimidazolium [B(C$_2$F$_5$)(CN)$_3$],
tetra-phenylphosphonium [C$_6$F$_5$BF(CN)$_2$].

The invention furthermore relates to compounds of formula (I-c)

$$M^{a+}[B(R_f)(CN)_3]_a^-  \quad (I\text{-}c)$$

in which,
$M^{a+}$ is an organic cation selected from the group comprising sulfonium, oxonium, ammonium, phosphonium, uronium, thiouronium, guanidinium cations or heterocyclic cations as described above
$R_f$ denotes straight-chain or branched perfluoroalkyl groups having 1 to 4 C atoms, C$_6$F$_5$, C$_6$H$_5$, partially fluorinated phenyl or phenyl which is monosubstituted or disubstituted by perfluoroalkyl groups having 1 to 4 C atoms, preferably denotes straight-chain or branched perfluoroalkyl groups having 1 to 4 C atoms or C$_6$F$_5$, and a denotes 1.

Specific examples of compounds of formula (I-c) are compounds selected from the group
1-ethyl-3-methylimidazolium [B(CF$_3$)(CN)$_3$],
1-ethyl-3-methylimidazolium [B(C$_2$F$_5$)(CN)$_3$].

The compounds of formula (I) may be synthesized through reaction of an alkalimetal [B(R$_f$)F$_3$], e.g. a perfluoroalkyltrifluoroborate in case of R$_f$ being a perfluoroalkyl group, with trialkylsilylcyanide followed by a cation-exchange reaction to convert compounds of formula (I) in which $M^{a+}$ is an alkalimetal to to compounds of formula (I) in which $M^{a+}$ is another cation as defined above and R$_1$ has a meaning as described above.

Such cation-exchange reaction or metathesis reaction may be performed with a compound of formula MA,
in which
M denotes $M^{a+}$ as defined above but not including the alkali metal of the starting material of the alkalimetal trifluoroperfluoroalkylborate and
A is selected from the group of anions
F$^-$, Cl$^-$, Br$^-$, I$^-$, OH$^-$, [HF$_2$]$^-$, [CN]$^-$, [SCN]$^-$, [R$_1$COO]$^-$, [R$_1$SO$_3$]$^-$, [R$_2$COO]$^-$, [R$_2$SO$_3$]$^-$, [R$_1$OSO$_3$]$^-$, [SiF$_6$]$^{2-}$, [BF$_4$]$^-$, [SO$_4$]$^{2-}$, [HSO$_4$]$^{1-}$, [NO$_3$]$^-$, [(R$_1$)$_2$P(O)O]$^-$, [R$_1$P(O)O$_2$]$^{2-}$, [(R$_1$O)$_2$P(O)O]$^-$, [(R$_1$O)P(O)O$_2$]$^{2-}$, [(R$_2$)$_2$P(O)O]$^-$, [R$_2$P(O)O$_2$]$^{2-}$, tosylate, benzoate, oxalate, succinate, suberate, ascorbate, sorbate, tartrate, citrate, malate, malonate, the malonate optionally substituted with straight-chain or branched alkyl groups having 1 to 4 C atoms or [CO$_3$]$^{2-}$,
in which R$_1$ denotes independantly of each other H and/or a straight-chain or branched alkyl group having 1 to 12 C atoms and
R$_2$ denotes independantly of each other a fluorinated or perfluorinated straight-chain or branched alkyl group having 1 to 12 C atoms or pentafluorophenyl and in which the salt MA is electrically neutral.

This process can be carried out on the air, preferably in dry atmosphere, for example under dry air, nitrogen or argon.

Alkalimetal perfluoroalkyltrifluoroborates or the compounds alkalimetal [B(R$_f$)F$_3$] in which R$_f$ has a meaning as described above, are in some cases commercially available or can be synthesised by known processes. Known processes for the preparation of compounds of alkalimetal perfluoroalkyltrifluoroborates are described, for example, in U.S. Pat. No. 7,208,626 B2; WO 2003/087020 (A1) and WO 2003/087113 (A1) or in R. D. Chambers et al., *J. Am. Chem. Soc.* 82 (1960), p. 5296-5301; H.-J-Frohn and V. V. Bardin, *Z. für Anorg. und Allg. Chemie*, 627 (2001), S. 15-16; G. A. Molander and G. P. Hoag, *Organometallics*, 22 (2003), p. 3313-3315 or Zhi-Bin Zhou et al., *J. of Fluorine Chem.*, 123 (2003), p. 127-131].

Trialkylsilylcyanide in which the alkyl groups independently denotes straight-chain or branched alkyl groups having 1 to 4 C atoms are in some cases commercially available or can be synthesised by known processes. For example, it is possible to generate trialkylsilylcyanide by reaction of alkalimetalcyanide with trialkylsilylchloride in the presence of alkalimetaliodide and optionally elemental iodine.

The alkyl groups of trialkylsilylcyanide may be the same or different. Preferably, they are the same. Examples of trialkylsilylcyanides are such as trimethylsilylcyanide, triethylsilylcyanide, dimethylethylsilylcyanide, triisopropylsilylcyanide, tripropylsilylcyanide or tributylsilylcyanide. Particularly preferred is the use of trimethylsilylcyanide.

The process for the preparation of compounds of the formula (I) in which $M^{a+}$ is an alkali metal cation may be carried out in an organic solvent or in the absence of an organic solvent if one starting material is liquid at the reaction temperature such as at a temperature between 10° C. and 200° C. or in the presence of microwave irradiation. It is preferred to use microwave irradiation.

Useful organic solvents are for example, acetonitrile, dimethoxyethane, tetrahydrofurane. The process for the preparation of compounds of formula (I) in which $M^{a+}$ is an alkali metal cation is preferably carried out without a solvent.

The process for the preparation of compounds of formula (I) in which the cation is an organic cation or an inorganic cation other than an alkalimetal cation is a metathesis reaction (salt-exchange reaction) in which the cation will be replaced as commonly known.

The present invention will now be illustrated, without limiting its scope, by way of the following examples:

EXAMPLE 1

K[CF$_3$BF$_2$(CN)]

Potassium trifluorotrifluoromethylborate, K[CF$_3$BF$_3$] (3.0 g, 17.0 mmol), is weighed out into a cylindrical reaction vessel with a glass valve and PTFE spindle (Young, London) and a magnetic stirrer bar. Trimethyl silylcyanide (6.0 mL, 45.0 mmol) is added in the presence of an argon atmosphere. The reaction mixture is stirred at room temperature for 20 hours. All volatile constituents are removed in vacuo. The unreacted trimethylsilyl cyanide (3.0 mL, 22.5 mmol) is recovered through fractionated distillation. The solid residue is dissolved in tetrahydrofurane. Addition of dichloromethane causes the precipitation of K[CF$_3$BF$_2$CN] which is filtered off and dried in vacuo. The yield based on potassium trifluorotrifluoromethylborate is 3.0 g (16.4 mmol, 96%).

Decomposition from 200° C.

Raman spectroscopy: ν (CN)=2226 cm$^{-1}$.

$^{11}$B-NMR: δ, ppm=−3.8 tq (1B), $^1J_{F,B}$=49.0 Hz, $^2J_{F,B}$=34.5 Hz.

$^{19}$F-NMR: δ, ppm=−77.4 q (CF$_3$, 3F), $^2J_{F,B}$=34.5 Hz; −169.1 q (BF$_2$, 2F), $^1J_{F,B}$=49.3 Hz

Analogously, K[C$_2$F$_5$BF$_2$(CN)], K[CF$_3$BF(CN)$_2$] and K[C$_2$F$_5$BF(CN)$_2$] may be prepared. For compounds of formula (I) with a pentafluoroethyl group, the starting material is potassium trifluoropentafluoroborate. Compounds of formula (I) with an alkali metal cation and [CF$_3$BF(CN)$_2$] or [C$_2$F$_5$BF(CN)$_2$] anions may be prepared at a reaction temperature of 110° C. to 200° C. or with microwave irradiation (200 W) followed by salt-exchange reaction as described e.g. in example 2.

Analogously, compounds of formula (I) with an alkali metal cation and [CF$_3$B(CN)$_3$] or [C$_2$F$_5$B(CN)$_3$] may be prepared with microwave irradiation above 200 W followed by salt-exchange reaction as described e.g. in example 2.

EXAMPLE 2

1-Ethyl-3-methylimidazoliumcyanodifluorotrifluoromethylborate —[C$_6$H$_{11}$N$_2$][CF$_3$BF$_2$(CN)]

K[CF$_3$BF$_2$(CN)] (5.9 g, 32.5 mmol), prepared as described in Example 1, is dissolved in deionized water (20 mL) and 1-ethyl-3-methylimidazoliumchloride, [emim]Cl (5.0 g, 34.1 mmol) dissolved in deionized water (20 mL) is added by the mixing of the reaction mixture with the magnetic stirring bar. The ionic liquid is separated, washed with deionized water and dried in vacuo at 50° C. The yield of liquid 1-ethyl-3-methylimidazoliumcyanodifluorotrifluoromethylborate is 5.7 g (22.4 mmol), 69% based on the potassium cyanodifluorotrifluoromethylborate employed.

Melting point: 13° C.

Water content (Karl-Fischer Titration) is 40 ppm.

Dynamic viscosity (20° C.): 16.5 mPa·s.

$^1$H-NMR: δ, ppm=1.5 t (CH$_3$, 3H), $^3J_{H,H}$=7 Hz; 4.0 s (CH$_3$, 3H); 4.3 q (CH$_2$, 2H), $^3J_{H,H}$=7 Hz; 7.6 m (CH, 1H); 7.7 m (CH, 1H); 8.9 br.s (CH, 1H).

$^{13}$C{$^1$H}-NMR (cation): δ, ppm=136.8 s (1C), 124.6 s (1C), 122.9 s (1C), 45.6 s (1C), 36.5 s (1C), 15.4 s (1C).

All other compounds which build the following electrolyte formulations are synthesized analogously.

EXAMPLE 3

Formulations and Device

The following electrolyte formulations are synthesized to demonstrate the unexpected advantage of electrolyte formulations according to the invention relative to electrolyte formulations of the prior art containing the tetracyanoborate anion if the same cation is used.

A) The Ionic Liquids Used in One Measurement:

| | cation | anion |
|---|---|---|
| 1 | 1-ethyl-3-methylimidazolium<br>H$_3$C—N⟨⟩N$^+$—CH$_3$ | Tetracyanoborate = TCB<br>NC—B$^-$(CN)$_3$ |
| 2 | 1-ethyl-3-methylimidazolium<br>H$_3$C—N⟨⟩N$^+$—CH$_3$ | Perfluoromethylcyanodifluoroborate |
| 3 | 1-ethyl-3-methylimidazolium<br>H$_3$C—N⟨⟩N$^+$—CH$_3$ | Perfluoromethyldicyanofluoroborate |
| | 1-ethyl-3- | Perfluoroethylcyano |

-continued

| | cation | anion |
|---|---|---|
| 4 | methylimidazolium (H3C-N∕=∖N+-CH3) | difluoroborate (F,F,F,F,B-,CN) |
| 5 | 1-ethyl-3-methylimidazolium (H3C-N∕=∖N+-CH3) | Perfluoroethyl dicyanofluoroborate (F,F,F,F,F,B-,NC,CN) |

The electrolyte formulations are prepared through mixing of one or more of 1,3-dimethylimidazolium iodide (mmimI), 1-ethyl-3-methylimidazolium iodide (emimI) and the ionic liquid 1 to 5 together with iodine, N-butylbenzimidazole (NBB) and guanidinium thiocyanate (guaSCN) in the molar ratio as listed below. It may be necessary to apply heat up to 120° C. to make the electrolyte formulation homogeneous.

Electrolyte formulation 1 given in molar ratio: 36 mmimI, 36 emimI, 5 $I_2$, 48 emimTCB, 2 guaSCN, 10 NBB;

Electrolyte formulation 2 given in molar ratio: 36 mmimI, 36 emimI, 5 $I_2$, 48 emim[B(CF$_3$)CNF$_2$], 2 guaSCN, 10 NBB;

Electrolyte formulation 3 given in molar ratio: 36 mmimI, 36 emimI, 5 $I_2$, 48 emim[B(CF$_3$)(CN)$_2$F], 2 guaSCN, 10 NBB;

Electrolyte formulation 4 given in molar ratio: 36 mmimI, 36 emimI, 5 $I_2$, 48 emim[B(C$_2$F$_5$)(CN)F$_2$], 2 guaSCN, 10 NBB;

Electrolyte formulation 5 given in molar ratio: 36 mmimI, 36 emimI, 5 $I_2$, 48 emim[B(C$_2$F$_5$)(CN)F$_2$], 2 guaSCN, 10 NBB.

TABLE 1

Electrolyte formulations employed in the present invention for devices fabricated as described below

| Electrolyte formulation | DSC efficiency at 25° C. under AM1.5 | DSC efficiency at 12° C. under AM1.5 |
|---|---|---|
| 1* | 5.2 ± 0.5% | 3.5 ± 0.5% |
| 2 | 5.8 ± 0.8% | |
| 3 | 6.0 ± 0.8% | |
| 4 | 5.5 ± 0.3% | 4.6 ± 0.2% |
| 5 | 5.4 ± 0.3% | 4.6 ± 0.1% |

*not according to the invention

Table 1 documents that electrolytes comprising the indicated anions perform better than electrolytes comprising TCB as anion if the same cation is used.

The compounds mmimI, emimI, $I_2$, NBB and guaSCN are commercially available or are synthesized according to known literature such as Bonhote, P et al. *Inorg. Chem.* 1996, 35, 1168-1178.

The dye sensitized solar cells are fabricated as disclosed in U.S. Pat. No. 5,728,487 or WO 2007/093961:

A double-layer, mesoporous TiO$_2$ electrode was prepared as disclosed in Wang P et al., *J. Phys. Chem. B* 2003, 107, 14336, in particular page 14337, in order to obtain a photoanode consisting of a double layer structure. To prepare a transparent nanoporous TiO$_2$ electrode, a screen printing paste containing terpineol solvent and nanoparticulate TiO$_2$ of anatase phase with 20 nm diameter was deposited on a transparent conductive substrate to 5 mm×5 mm squared shape by using a hand printer. The paste was dried for 10 minutes at 120 degrees Celsius. Another screen printing paste containing TiO$_2$ with 400 nm diameter was then deposited on top of the nanoporous layer to prepare an opaque layer. The double layer film was then sintered at 500 degrees Celsius for an hour with the result of an underlying transparent layer (7 microns thick) and a top opaque layer (4 microns thick). After sintering, the electrode was immersed in 40 mM aqueous solution of TiCl$_4$ (Merck) for 30 minutes at 70 degrees Celsius and then rinsed with pure water sufficiently. Thus TiCl$_4$-treated electrode was dried at 500 degrees Celsius for 30 minutes just before dye sensitization. The electrode was dipped into a 0.3 mM Z907 dye solution of acetonitrile (Merck HPLC grade) and tert-butyl alcohol (Merck), v:v=1:1 for 60 hours at 19 degrees Celsius. The counter electrode was prepared with thermal pyrolysis method as disclosed in the reference above. A droplet of 5 mM solution of platinic acid (Merck) was casted at 8 μl/cm2 and dried on a conductive substrate. The dye sensitized solar cell was assembled by using 30 micron thick Bynel (DuPont, USA) hot-melt film to seal up by heating. The internal space was filled with each of the electrolyte formulations as described above to produce the corresponding devices.

The dye Z907 is an amphiphilic ruthenium sensitizer Ru(2, 2'-bipyridine 4,4'-dicarboxylic acid) (4,4'-dinonyl-2,2'-bipyridine)(NCS)$_2$ or [Ru(H2dcbpy)(dnbpy)(NCS)$_2$].

B) The Ionic Liquids Used in Another Measurement:

| | cation | anion |
|---|---|---|
| 1* | 1-ethyl-3-methylimidazolium emim | Tetracyanoborate = TCB |
| 7* | (H3C-N+(pyrrolidine ring)-CH3) | TCB |
| 8 | (H3C-N∕=∖N+-CH3, with CH3 at 2-position) | [B(CF$_3$)CNF$_2$] |
| 9 | (H3C-N∕=∖N+-CH3, with CH3 at 2-position) | [B(C$_2$F$_5$)CNF$_2$] |
| 10 | (H3C-N∕=∖N+-CH2CH2-O-CH3) | [B(C$_2$F$_5$)CNF$_2$] |
| 11 | (H3C-N∕=∖N+-CH2CH2CH2-CH3) | [B(C$_2$F$_5$)CNF$_2$] |

-continued

| | cation | anion |
|---|---|---|
| 12 | (1-methyl-1-propylpyrrolidinium) | $[B(C_2F_5)CNF_2]$ |
| 13 | (tributylmethylammonium) | $[B(C_2F_5)CNF_2]$ |
| 14 | (tributylmethylphosphonium) | $[B(C_2F_5)CNF_2]$ |
| 15 | (diethylmethylsulfonium) | $[B(C_2F_5)CNF_2]$ |
| 16 | (S-ethyl-N,N,N',N'-tetramethylisothiouronium) | $[B(C_2F_5)CNF_2]$ |
| 17 | (1-methyl-3-(2-methoxyethyl)imidazolium) | $[B(C_2F_5)(CN)_2F]$ |
| 18 | (1-butyl-3-methylimidazolium) | $[B(C_2F_5)(CN)_2F]$ |
| 19 | (1-methyl-1-propylpyrrolidinium) | $[B(C_2F_5)(CN)_2F]$ |
| 20' | (1-allyl-3-methylimidazolium) / I | emim$[B(C_2F_5)(CN)_2F]$ |
| 21' | (1-allyl-2,3-dimethylimidazolium) / I | emim$[B(C_2F_5)(CN)_2F]$ |
| 22' | (1-methyl-3-propynylimidazolium) / I | emim$[B(C_2F_5)(CN)_2F]$ |

'used as a mixture, *not according to the invention

The electrolyte formulations are prepared analogously as disclosed in 3A with the given molar ratio and the compounds as indicated below. The fabrication of the devices were done as described above—however the results are lower than expected which can be seen from the comparison data for emimTCB which merely shows an efficiency of 4.1% of electrolyte formulation 1 and electrolyte formulation 6 which is below all measurements done so far—which means this study of ionic liquids needs to be interpreted in the light of this comparison to TCB.

Electrolyte formulation 1 given in molar ratio: 36 mmimI, 36 emimI, 5 $I_2$, 48 emimTCB, 2 guaSCN, 10 NBB;

Electrolyte formulation 1* given in molar ratio: 60 emimI, 5 $I_2$, 60 emimTCB, 2 guaSCN, 10 NBB;

Electrolyte formulation 7 given in molar ratio: 60 emimI, 5 $I_2$, 60 bmpITCB, 2 guaSCN, 10 NBB;

Electrolyte formulation 8 given in molar ratio: 60 emimI, 5 $I_2$, 60 emmim[B(CF$_3$)(CN)F$_2$] (ionic liquid 8), 2 guaSCN, 10 NBB;

Electrolyte formulation 9 given in molar ratio: 60 emimI, 5 $I_2$, 60 emmim[B(C$_2$F$_5$)(CN)F$_2$] (ionic liquid 9), 2 guaSCN, 10 NBB;

Electrolyte formulation 10 given in molar ratio: 60 emimI, 5 $I_2$, 60 moemim[B(C$_2$F$_5$)(CN)F$_2$] (ionic liquid 10), 2 guaSCN, 10 NBB;

Electrolyte formulation 11 given in molar ratio: 60 emimI, 5 $I_2$, 60 bmim[B(C$_2$F$_5$)(CN)F$_2$] (ionic liquid 11), 2 guaSCN, 10 NBB;

Electrolyte formulation 12 given in molar ratio: 60 emimI, 5 $I_2$, 60 bmpl[B(C$_2$F$_5$)(CN)F$_2$] (ionic liquid 12), 2 guaSCN, 10 NBB;

Electrolyte formulation 13 given in molar ratio: 60 emimI, 5 $I_2$, 60 tributylmethylammonium[B(C$_2$F$_5$)(CN)F$_2$] (ionic liquid 13), 2 guaSCN, 10 NBB;

Electrolyte formulation 14 given in molar ratio: 60 emimI, 5 $I_2$, 60 tributylmethylphosphonium[B(C$_2$F$_5$)(CN)F$_2$] (ionic liquid 14), 2 guaSCN, 10 NBB;

Electrolyte formulation 15 given in molar ratio: 60 emimI, 5 $I_2$, 60 diethylmethylsulfonium[B(C$_2$F$_5$)(CN)F$_2$] (ionic liquid 15), 2 guaSCN, 10 NBB;

Electrolyte formulation 16 given in molar ratio: 60 emimI, 5 $I_2$, 60 S-ethyl-N,N,N',N'-tetramethylisothiouronium[B(C$_2$F$_5$)(CN)F$_2$] (ionic liquid 16), 2 guaSCN, 10 NBB;

Electrolyte formulation 17 given in molar ratio: 60 emimI, 5 $I_2$, 60 moemim[B(C$_2$F$_5$)(CN)$_2$F] (ionic liquid 17), 2 guaSCN, 10 NBB;

Electrolyte formulation 18 given in molar ratio: 60 emimI, 5 $I_2$, 60 bmim[B(C$_2$F$_5$)(CN)$_2$F] (ionic liquid 18), 2 guaSCN, 10 NBB;

Electrolyte formulation 19 given in molar ratio: 60 emimI, 5 $I_2$, 60 bmpl[B(C$_2$F$_5$)(CN)$_2$F] (ionic liquid 19), 2 guaSCN, 10 NBB;

Electrolyte formulation 20 given in molar ratio: 60 1-allyl-3-methylimidazoliumI, 5 $I_2$, 60 emim[B(C$_2$F$_5$)(CN)$_2$F], 2 guaSCN, 10 NBB;

Electrolyte formulation 21 given in molar ratio: 60 1-allyl-2,3-dimethylimidazoliumI, 5 $I_2$, 60 emim[B(C$_2$F$_5$)(CN)$_2$F], 2 guaSCN, 10 NBB;

Electrolyte formulation 22 given in molar ratio: 60 1-methyl-3-propynylimidazoliumI, 5 $I_2$, 60 emim[B(C$_2$F$_5$)(CN)$_2$F], 2 guaSCN, 10 NBB;

TABLE 2

Electrolyte formulations employed in the present invention for devices fabricated as described before

| Electrolyte formulation | DSC efficiency at 25° C. under AM1.5 |
|---|---|
| 1* | 4.1% ± 0.1% |
| 1** | 4.1% ± 0.1% |
| 7* | 3.3% ± 0.3% |
| 8 | 3.2% ± 0.3% |
| 9 | 3.3% ± 0.3% |

TABLE 2-continued

Electrolyte formulations employed in the present invention for devices fabricated as described before

| Electrolyte formulation | DSC efficiency at 25° C. under AM1.5 |
|---|---|
| 10 | 3.1 ± 0.3% |
| 11 | 3.6 ± 0.3% |
| 12 | 3.0 ± 0.7% |
| 13 | 0.9 ± 0.4% |
| 14 | 1.5 ± 0.8% |
| 15 | 3.7 ± 0.3% |
| 16 | 2.5 ± 0.4% |
| 17 | 3.3 ± 0.3% |
| 18 | 2.8 ± 0.3% |
| 19 | 3.5 ± 0.3% |
| 20 | 3.9 ± 0.1% |
| 21 | 3.1 ± 0.3% |
| 22 | 0.1 ± 0.1% |

*not according to the invention

Table 2 documents that electrolytes comprising the indicated anions perform better or similar than electrolytes comprising TCB as anion if the same cation is used.

EXAMPLE 4

Characteristics of the Dye Sensitized Solar Cells According to Example 3A

The measurements of photocurrent-voltage curves are carried out under Air Mass 1.5 simulated sunlight (AM 1.5) with temperature control. A photomask of 4 mm×4 mm is placed on top of the devices fabricated according to example 3 to define the light projection area. The cell gap is in the range of 25 to 30 micron.

Energy conversion efficiency is generally the ratio between the useful output of an energy conversion machine and the input of light radiation, in energy terms, determined by using adjustable resistant load to optimize the electric power output.

EXAMPLE 5

Electrochemical Impedance Spectroscopy (EIS)

Figure 1:
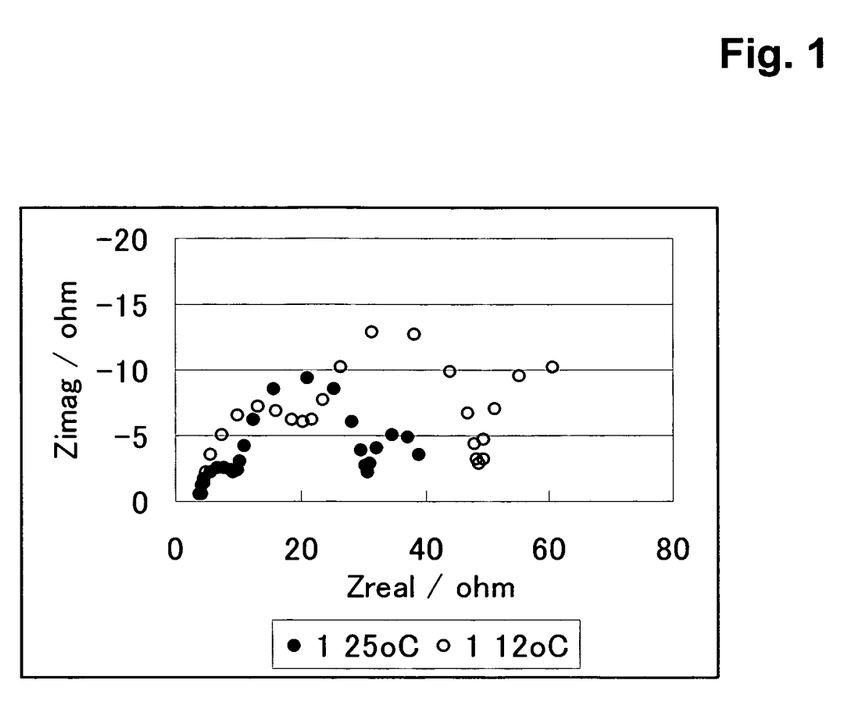
FIG. 1 gives the impedance spectrum of device 1 containing electrolyte formulation 1 as comparative example as prepared according to example 3A.
Figure 2:
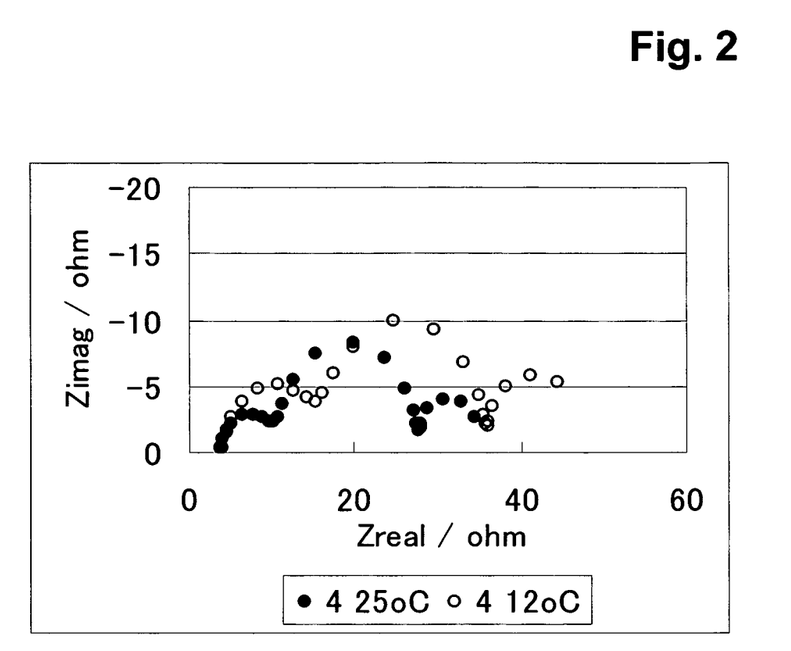
FIG. 2 gives the impedance spectrum of device 4 containing electrolyte formulation 4 as prepared according to example 3A.
Figure 3:
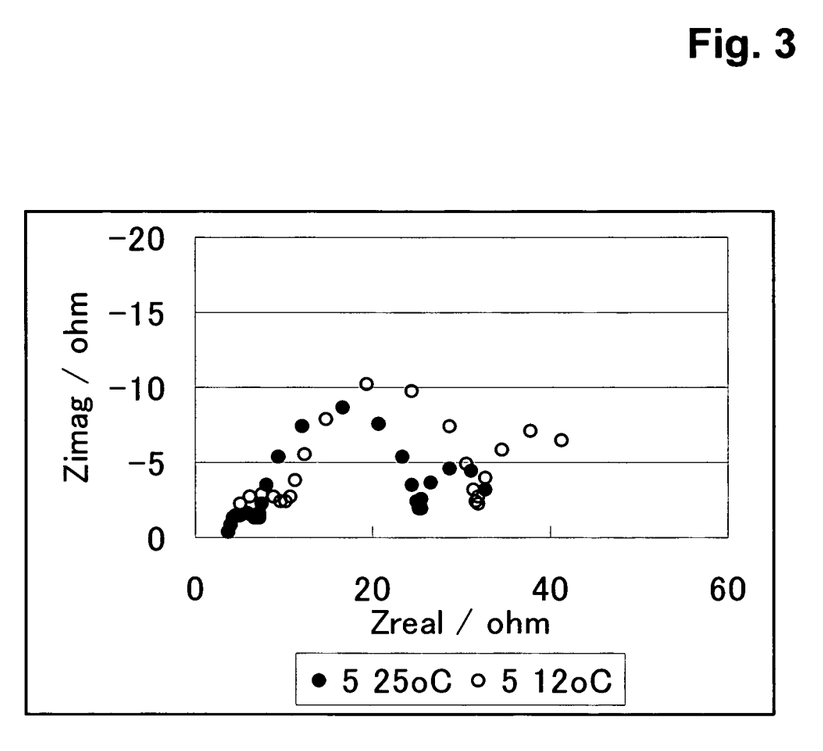
FIG. 3 gives the impedance spectrum of device 5 containing electrolyte formulation 5 as prepared according to example 3A.

The impedance of the devices 1, 4 and 5 fabricated according to example 3A are measured at 12° C. and 25° C. under AM1.5 by using Gamry R600 impedance analyzer to identify the factor responsible for the photovoltaic performance differences.

FIG. 1 gives the impedance spectrum of device 1 containing electrolyte formulation 1 as comparative example.

FIG. 2 gives the impedance spectrum of device 4 containing electrolyte formulation 4.

FIG. 3 gives the impedance spectrum of device 5 containing electrolyte formulation 5.

Table 3 shows impedances and their characteristic frequencies for devices 1, 4 and 5 measured at 12 and 25 degrees Celsius under AM1.5.

| | Temperature | Charge Transfer Resistance | | Nernst Diffusion Resistance | |
|---|---|---|---|---|---|
| | ° C. | $Z_{CT}$ [Ω] | $f_{CT}$ [Hz] | $Z_{ND}$ [Ω] | $f_{ND}$ [Hz] |
| 1 | 12 | 4.4 | $8 \times 10^3$ | 48 | 0.1 |
|   | 25 | 3.9 | $2 \times 10^4$ | 25 | 0.3 |
| 2 | 25 | 3.6 | $1 \times 10^4$ | 25 | 0.3 |
| 3 | 25 | 3.2 | $3 \times 10^4$ | 21 | 0.6 |
| 4 | 12 | 4.0 | $1 \times 10^4$ | 36 | 0.2 |
|   | 25 | 3.7 | $2 \times 10^4$ | 25 | 0.3 |
| 5 | 12 | 3.9 | $1 \times 10^4$ | 32 | 0.2 |
|   | 25 | 3.5 | $2 \times 10^4$ | 24 | 0.3 |

It can be seen that replacement of TCB with the anions of the invention reduces charge transfer resistance significantly making perfluoroalkylcyanofluoroborate-based electrolyte formulations for DSC work at 12 degrees Celsius.

EXAMPLE 6

The following electrolyte formulations are synthesized according to example 3A and used as electrolytes in DSSC test cells as prepared according to example 3A:

Electrolyte formulation 23 given in molar ratio: 36 mmimI, 36 emimI, 5 $I_2$, 72 bmpITCB, 2 guaSCN, 10 NBB;

Electrolyte formulation 24 given in molar ratio: 36 mmimI, 36 emimI, 5 $I_2$, 72 bmpI[B($C_2F_5$)(CN)$_2$F], 2 guaSCN, 10 NBB;

Electrolyte formulation 25 given in molar ratio: 36 mmimI, 36 emimI, 5 $I_2$, 72 bmpI[B($C_2F_5$)(F)$_2$CN], 2 guaSCN, 10 NBB;

Electrolyte formulation 26 given in molar ratio: 36 mmimI, 36 emimI, 5 $I_2$, 72 diethylmethylsulfonuim[B($C_2F_5$)(F)$_2$CN], 2 guaSCN, 10 NBB.

Table 4 summarizes the results of the measurements of the above cited electrolyte formulations according to example 4: η=DSC efficiency

| Electrolyte | $J_{SC}$ [mAcm$^{-2}$] | $V_{OC}$ [V] | FF | η [%] |
|---|---|---|---|---|
| 23* | 8.18 | 0.70 | 0.58 | 3.47 |
| 23* | 8.55 | 0.75 | 0.55 | 3.48 |
| 24 | 8.39 | 0.72 | 0.64 | 3.88 |
| 24 | 8.30 | 0.73 | 0.61 | 3.73 |
| 25 | 9.20 | 0.73 | 0.68 | 3.94 |
| 25 | 8.71 | 0.72 | 0.66 | 3.92 |
| 26 | 8.99 | 0.71 | 0.67 | 4.28 |
| 26 | 8.92 | 0.71 | 0.67 | 4.23 |

*not according to the invention

The invention claimed is:

1. An electrolyte formulation comprising at least one compound of formula (I)

$$M^{a+}[B(R_f)(CN)_x(F)_y]_a^- \qquad (I)$$

in which $M^{a+}$ is an inorganic or organic cation, $R_f$ denotes straight-chain or branched perfluoroalkyl groups having 1 to 4 C atoms, $C_6F_5$, partially fluorinated phenyl or phenyl which is monosubstituted or disubstituted by perfluoroalkyl groups having 1 to 4 C atoms,
a is 1, 2, 3 or 4,
x is 1, 2 or 3,
y is 0, 1 or 2 and
x+y is 3.

2. The electrolyte formulation according to claim 1 characterized in that x in formula (I) is 1 and y is 2.

3. The electrolyte formulation according to claim 1 characterized in that x in formula (I) is 2 and y is 1.

4. The electrolyte formulation according to claim 1 characterized in that x in formula (I) is 3 and y is 0.

5. The electrolyte formulation according to claim 1 characterized in that $M^{a+}$ in formula (I) is a metal cation.

6. The electrolyte formulation according to claim 1 characterized in that $M^{a+}$ is an organic cation selected from: sulfonium, oxonium, ammonium, phosphonium, uronium, thiouronium, guanidinium cations or heterocyclic cations.

7. The electrolyte formulation according to claim 1 comprising the compound of formula (I) in a molar concentration of from 0.1 to 5.5 M.

8. An electrochemical and/or optoelectronic device comprising an electrolyte formulation according to claim 1.

9. The device according to claim 8 characterized in that it is a photovoltaic cell, a capacitor, a light emitting device, an electrochromic or photo-electrochromic device, an electrochemical sensor and/or a biosensor.

10. The device according to claim 8 which is a dye sensitized solar cell.

11. The device according to claim 10 comprising a semiconductor, the electrolyte formulation, and a counter electrode.

12. A compound of formula (I-a)

$$M^{a+}[B(R_f)(CN)(F)_2]_a^-  \qquad (I\text{-}a)$$

in which,
$M^{a+}$ is an organic cation selected from: sulfonium, oxonium, ammonium, phosphonium, uronium, thiouronium, guanidinium cations or heterocyclic cations,
$R_f$ denotes straight-chain or branched perfluoroalkyl groups having 1 to 4 C atoms, $C_6F_5$, $C_6H_5$, partially fluorinated phenyl or phenyl which is monosubstituted or disubstituted by perfluoroalkyl groups having 1 to 4 C atoms and a denotes 1.

13. A compound according to claim 12, which is selected from:

1-ethyl-3-methylimidazolium [B($C_2F_5$)CN$F_2$],
1-ethyl-2,3-dimethylimidazolium [B($C_2F_5$)CN$F_2$],
1-(2-methoxyethyl)-3-methylimidazolium [B($C_2F_5$)CN$F_2$],
1-butyl-3-methylimidazolium [B($C_2F_5$)CN$F_2$],
1-butyl-1-methylpyrrolidinium [B($C_2F_5$)CN$F_2$],
tributyl-methylammonium [B($C_2F_5$)CN$F_2$],
tetra-n-butylammonium [B($C_2F_5$)CN$F_2$],
tributyl-methylphosphonium [B($C_2F_5$)CN$F_2$],
tetra-phenylphosphonium [B($C_2F_5$)CN$F_2$],
diethyl-methylsulfonium [B($C_2F_5$)CN$F_2$],
S-ethyl-N,N,N',N'-tetramethylisothiouronium [B($C_2F_5$)CN$F_2$],
1-ethyl-3-methylimidazolium [B($CF_3$)CN$F_2$],
1-ethyl-2,3-dimethylimidazolium [B($CF_3$)CN$F_2$],
1-(2-methoxyethyl)-3-methylimidazolium [B($CF_3$)CN$F_2$],
1-butyl-3-methylimidazolium [B($CF_3$)CN$F_2$],
1-butyl-1-methylpyrrolidinium [B($CF_3$)CN$F_2$],
tributyl-methylammonium [B($CF_3$)CN$F_2$],
tetra-n-butylammonium [B($CF_3$)CN$F_2$],
tributyl-methylphosphonium [B($CF_3$)CN$F_2$],
tetra-phenylphosphonium [B($CF_3$)CN$F_2$],
diethyl-methylsulfonium [B($CF_3$)CN$F_2$], and
ethyl-tetramethylisothiouronium [B($CF_3$)CN$F_2$].

14. A compound which is selected from:
1-ethyl-3-methylimidazolium [B($C_2F_5$)(CN)$_2$F],
1-(2-methoxyethyl)-3-methylimidazolium [B($C_2F_5$)(CN)$_2$F],
1-butyl-3-methylimidazolium [B($C_2F_5$)(CN)$_2$F],
1-butyl-1-methylpyrrolidinium [B($C_2F_5$)(CN)$_2$F],
tetra-phenylphosphonium [B($C_2F_5$)(CN)$_2$F],
tetra-n-butylammonium [B($C_2F_5$)(CN)$_2$F],
1-ethyl-3-methylimidazolium [B($CF_3$)(CN)$_2$F],
1-(2-methoxyethyl)-3-methylimidazolium [B($CF_3$)(CN)$_2$F],
tetra-phenylphosphonium [B($CF_3$)(CN)$_2$F],
1-butyl-3-methylimidazolium [B($CF_3$)(CN)$_2$F],
1-butyl-1-methylpyrrolidinium [B($CF_3$)(CN)$_2$F],
1-ethyl-3-methylimidazolium [B($C_2F_5$)CN$F_2$],
1-ethyl-2,3-dimethylimidazolium [B($C_2F_5$)(CN)$_3$],
tetra-phenylphosphonium [$C_6F_5$BF(CN)$_2$],
1-ethyl-3-methylimidazolium [B($CF_3$)(CN)$_3$], and
1-ethyl-3-methylimidazolium [B($C_2F_5$)(CN)$_3$].

* * * * *